(12) United States Patent
Fowler et al.

(10) Patent No.: US 6,486,186 B2
(45) Date of Patent: *Nov. 26, 2002

(54) THIAZOLE COMPOUNDS AS CYCLIC AMP-SPECIFIC PHOSPHODIESTERASE INHIBITORS AND METHOD OF USING THE SAME

(75) Inventors: Kerry W. Fowler, Seattle, WA (US); Joshua Odingo, Bothell, WA (US)

(73) Assignee: ICOS Corporation, Bothell, WA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/954,934

(22) Filed: Sep. 18, 2001

(65) Prior Publication Data

US 2002/0042435 A1 Apr. 11, 2002

Related U.S. Application Data

(63) Continuation of application No. 09/723,091, filed on Nov. 27, 2000, now Pat. No. 6,313,156.
(60) Provisional application No. 60/171,950, filed on Dec. 13, 1999.

(51) Int. Cl.[7] ............................................. A61K 31/427
(52) U.S. Cl. ...................................... 514/365; 514/370
(58) Field of Search .................................. 514/365, 370

(56) References Cited

U.S. PATENT DOCUMENTS

| | | | |
|---|---|---|---|
| 5,026,715 A | 6/1991 | Lamattina et al. | 514/326 |
| 5,665,754 A | 9/1997 | Feldman et al. | 514/397 |
| 5,998,428 A | 12/1999 | Barnette et al. | 514/285 |
| 6,313,156 B1 * | 11/2001 | Fowler et al. | 514/370 |

FOREIGN PATENT DOCUMENTS

| | | | |
|---|---|---|---|
| EP | 0 025 232 | 3/1981 | C07D/417/02 |
| EP | 0 671 389 | 9/1995 | C07D/207/08 |
| WO | WO 95/08534 | 3/1995 | C07D/207/16 |

OTHER PUBLICATIONS

J.E. Schultz et al., *Naunyn–Schmiedeberg's Arch Pharmacol*, 333, pp. 23–30 (1986).
Z. Ma et al., *Tetrahedron:Asymmetry*, vol. 8, No. 6, pp. 883–887 (1997).
A. Robichaud et al., *Neuropharmacology*, 38, pp. 289–297 (1999).
R.A. Allen et al., *Biochemical Pharmacology*, vol. 57, pp. 1375–1382 (1999).
J. Beavo et al., "Cyclic nucleotide phosphodiesterases: Structure, regulation and drug action," Wiley and Sons, Chichester, pp. 3–14 (1990).
T.J. Torphy et al., *Drug News and Perspectives*, 6, pp. 203–214 (1993).
M.A. Giembycz et al., *Clin. Exp. Allergy*, 22, pp. 337–344 (1992).
J. Semmler et al., *Int. J. Immunopharmacol.*, 15, pp. 409–413 (1993).
K.L. Molnar–Kimber et al., *Mediators of Inflammation*, 1, pp. 411–417 (1992).
M.W. Verghese et al., *J. Mol. Cell. Cardiiol.*, 21 (Suppl. 2), S61 (1989).
C.P. Nielson et al., *J. Allergy Immunol.*, 86, pp. 801–808 (1990).
P.T. Peachell et al., *J. Immunol.*, 148, pp. 2503–2510 (1992).
G. Dent et al., *J. Pharmacol.*, 103, pp. 1339–1346 (1991).
S.A. Robicsek et al., *Biochem. Pharmacol.*, 42, pp. 869–877 (1991).
H.S. Dhillon et al., *J. Neurotrauma*, 12, pp. 1035–1043 1995).
N. Suttorp et al., *J. Clin. Invest.*, 91, pp. 1421–1428 (1993).
M.R. Bristow et al., *Circulation*, 97, pp. 1340–1341 (1998).
G. Poli et al., *Proc. Natl. Acad. Sci. USA*, 87, pp. 782–785 (1990).
P. Orosz et al., *J. Exp. Med.*, 177, pp. 1391–1398 (1993).
M. Mentz et al., *Blood*, 88, pp. 2172–2182 (1996).
S. Takeda et al., *Kidney Int.*, 37, p. 362 (1990).
D. Chabardea et al., *Kidney Int.*, 35, p. 494 (1989).
C.D. Nicholson, *Psychopharmacology*, 101, p. 147 (1990).
F. Eckmann et al., *Curr. Ther. Res.*, 43, p. 291 (1988).
A. Klodzinska et al., *Neuropharmacology*, 38, p. 1831 (1991).
H. Kato et al., *Eur. J. Pharmacol.*, 272, p. 107 (1995).
G. Gardos et al., *J. Clin. Pharmocol.*, 16, p. 304 (1976).
I. Shoulson et al., *Neurology*, 25, p. 722 (1975).
T. Hayakawa et al., *Clin. Exp. Pharmacol. Physiol.*, 26, p. 421 (1999).
R.D. Porsolt et al., *Eur. J. Pharmacol.*, 47, p. 379 (1978).
R.D. Porsolt et al., *Eur. J. Pharmacol.*, 57, p. 431 (1979).
L. Steru, *Psychopharmacology*, 85, p. 376 (1985).
M. Takahashi, *J. Neuroscience*, 19, p. 610 (1999).
D. Pinsky et al., *J. Clin. Invest.*, 92, pp. 2994–3002 (1993).
*Antidepressants: neurochemical, behavioral and clinical prospectives*, Enna, Malick, and Richelson, eds., Raven Press, pp. 121–139 (1981).

* cited by examiner

Primary Examiner—Laurel L. Stockton
(74) Attorney, Agent, or Firm—Marshall, Gerstein & Borun

(57) ABSTRACT

Novel compounds that are potent and selective inhibitors of PDE4, as well as methods of making the same, are disclosed. Use of the compounds in the treatment of inflammatory diseases and other diseases involving elevated levels of cytokines, as well as central nervous system (CNS) disorders, also is disclosed.

5 Claims, No Drawings

THIAZOLE COMPOUNDS AS CYCLIC AMP-SPECIFIC PHOSPHODIESTERASE INHIBITORS AND METHOD OF USING THE SAME

CROSS-REFERENCE TO RELATED APPLICATIONS

This application is a continuation of application Ser. No. 09/723,091, filed Nov. 27, 2000, now U.S. Pat. No. 6,313,156, which claims the benefit of provisional application Serial No. 60/171,950, filed Dec. 23, 1999.

FIELD OF INVENTION

The present invention relates to a series of compounds that are potent and selective inhibitors of cyclic adenosine 3', 5'-monophosphate specific phosphodiesterase (cAMP specific PDE). In particular, the present invention relates to a series of novel thiazole compounds that are useful for inhibiting the function of cAMP specific PDE, in particular, PDE4, as well as methods of making the same, pharmaceutical compositions containing the same, and their use as therapeutic agents, for example, in treating inflammatory diseases and other diseases involving elevated levels of cytokines and proinflammatory mediators.

BACKGROUND OF THE INVENTION

Chronic inflammation is a multi-factorial disease complication characterized by activation of multiple types of inflammatory cells, particularly cells of lymphoid lineage (including T lymphocytes) and myeloid lineage (including granulocytes, macrophages, and monocytes). Proinflammatory mediators, including cytokines, such as tumor necrosis factor (TNF) and interleukin-1 (IL-1), are produced by these activated cells. Accordingly, an agent that suppresses the activation of these cells, or their production of proinflammatory cytokines, would be useful in the therapeutic treatment of inflammatory diseases and other diseases involving elevated levels of cytokines.

Cyclic adenosine monophosphate (cAMP) is a second messenger that mediates the biologic responses of cells to a wide range of extracellular stimuli. When the appropriate agonist binds to specific cell surface receptors, adenylate cyclase is activated to convert adenosine triphosphate (ATP) to cAMP. It is theorized that the agonist induced actions of cAMP within the cell are mediated predominately by the action of cAMP-dependent protein kinases. The intracellular actions of cAMP are terminated by either a transport of the nucleotide to the outside of the cell, or by enzymatic cleavage by cyclic nucleotide phosphodiesterases (PDEs), which hydrolyze the 3'-phosphodiester bond to form 5'-adenosine monophosphate (5'-AMP). 5'-AMP is an inactive metabolite. The structures of cAMP and 5'-AMP are illustrated below.

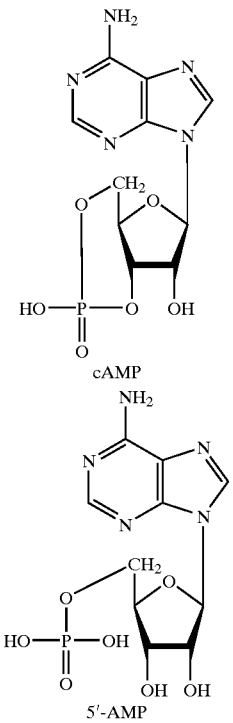

Elevated levels of cAMP in human myeloid and lymphoid lineage cells are associated with the suppression of cell activation. The intracellular enzyme family of PDEs, therefore, regulates the level of cAMP in cells. PDE4 is a predominant PDE isotype in these cells, and is a major contributor to cAMP degradation. Accordingly, the inhibition of PDE function would prevent the conversion of cAMP to the inactive metabolite 5'-AMP and, consequently, maintain higher cAMP levels, and, accordingly, suppress cell activation (see Beavo et al., "Cyclic Nucleotide Phosphodiesterases: Structure, Regulation and Drug Action,." Wiley and Sons, Chichester, pp. 3–14, (1990)); Torphy et al., *Drug News and Perspectives*, 6, pp. 203–214 (1993); Giembycz et al., *Clin. Exp. Allergy*, 22, pp. 337–344 (1992)).

In particular, PDE4 inhibitors, such as rolipram, have been shown to inhibit production of TNFα and partially inhibit IL-1β release by monocytes (see Semmler et al., Int. J. Immunopharmacol., 15, pp. 409–413, (1993); Molnar-Kimber et al., *Mediators of Inflammation*, 1, pp. 411–417, (1992)). PDE4 inhibitors also have been shown to inhibit the production of superoxide radicals from human polymorphonuclear leukocytes (see Verghese et al., *J. Mol. Cell. Cardiol.*, 21 (Suppl. 2), S61 (1989); Nielson et al., *J. Allergy Immunol.*, 86, pp. 801–808, (1990)); to inhibit the release of vasoactive amines and prostanoids from human basophils (see Peachell et al., *J. Immunol.*, 148, pp. 2503–2510, (1992)); to inhibit respiratory bursts in eosinophils (see Dent et al., *J. Pharmacol.*, 103, pp. 1339–1346, (1991)); and to inhibit the activation of human T-lymphocytes (see Robicsek et al., *Biochem. Pharmacol.*, 42, pp. 869–877, (1991)).

Inflammatory cell activation and excessive or unregulated cytokine (e.g., TNFα and IL-1β) production are implicated in allergic, autoimmune, and inflammatory diseases and disorders, such as rheumatoid arthritis, osteoarthritis, gouty arthritis, spondylitis, thyroid associated ophthalmopathy, Behcet's disease, sepsis, septic shock, endotoxic shock, gram negative sepsis, gram positive sepsis, toxic shock syndrome, asthma, chronic bronchitis, adult respiratory distress syndrome, chronic pulmonary inflammatory disease, such as chronic obstructive pulmonary disease, silicosis, pulmonary sarcoidosis, reperfusion injury of the myocardium, brain, and extremities, fibrosis, cystic fibrosis, keloid formation, scar formation, atherosclerosis, transplant rejection disorders, such as graft vs. host reaction and allograft rejection, chronic glomerulonephritis, lupus, inflammatory bowel disease, such as Crohn's disease and ulcerative colitis, proliferative lymphocyte diseases, such as leukemia, and inflammatory dermatoses, such as atopic dermatitis, psoriasis, and urticaria.

Other conditions characterized by elevated cytokine levels include brain injury due to moderate trauma (see Dhillon et al., *J. Neurotrauma*, 12, pp. 1035–1043 (1995); Suttorp et al., *J. Clin. Invest.*, 91, pp. 1421–1428 (1993)), cardiomyopathies, such as congestive heart failure (see Bristow et al., *Circulation*, 97, pp. 1340–1341 (1998)), cachexia, cachexia secondary to infection or malignancy, cachexia secondary to acquired immune deficiency syndrome (AIDS), ARC (AIDS related complex), fever myalgias due to infection, cerebral malaria, osteoporosis and bone resorption diseases, keloid formation, scar tissue formation, and pyrexia.

In particular, TNFα has been identified as having a role with respect to human acquired immune deficiency syndrome (AIDS). AIDS results from the infection of T-lymphocytes with Human Immunodeficiency Virus (HIV). Although HIV also infects and is maintained in myeloid lineage cells, TNF has been shown to upregulate HIV infection in T-lymphocytic and monocytic cells (see Poli et al., *Proc. Natl. Acad. Sci. USA*, 87, pp. 782–785, (1990)).

Several properties of TNFα, such as stimulation of collagenases, stimulation of angiogenesis in vivo, stimulation of bone resorption, and an ability to increase the adherence of tumor cells to endothelium, are consistent with a role for TNF in the development and metastatic spread of cancer in the host. TNFα recently has been directly implicated in the promotion of growth and metastasis of tumor cells (see Orosz et al., *J. Exp. Med.*, 177, pp. 1391–1398, (1993)).

PDE4 has a wide tissue distribution. There are at least four genes for PDE4 of which multiple transcripts from any given gene can yield several different proteins that share identical catalytic sites. The amino acid identity between the four possible catalytic sites is greater than 85%. Their shared sensitivity to inhibitors and their kinetic similarity reflect the functional aspect of this level of amino acid identity. It is theorized that the role of these alternatively expressed PDE4 proteins allows a mechanism by which a cell can differentially localize these enzymes intracellularly and/or regulate the catalytic efficiency via post translational modification. Any given cell type that expresses the PDE4 enzyme typically expresses more than one of the four possible genes encoding these proteins.

Investigators have shown considerable interest in the use of PDE4 inhibitors as anti-in-flammatory agents. Early evidence indicates that PDE4 inhibition has beneficial effects on a variety of inflammatory cells such as monocytes, macrophages, T-cells of the Th-1 lineage, and granulocytes. The synthesis and/or release of many proinflammatory mediators, such as cytokines, lipid mediators, superoxide, and biogenic amines, such as histamine, have been attenuated in these cells by the action of PDE4 inhibitors. The PDE4 inhibitors also affect other cellular functions including T-cell proliferation, granulocyte transmigration in response to chemotoxic substances, and integrity of endothelial cell junctions within the vasculature.

The design, synthesis, and screening of various PDE4 inhibitors have been reported. Methylxanthines, such as caffeine and theophylline, were the first PDE inhibitors discovered, but these compounds are nonselective with respect to which PDE is inhibited. The drug rolipram, an antidepressant agent, was one of the first reported specific PDE4 inhibitors. Rolipram, having the following structural formula, has a reported 50% Inhibitory Concentration ($IC_{50}$) of about 200 nM (nanomolar) with respect to inhibiting recombinant human PDE4.

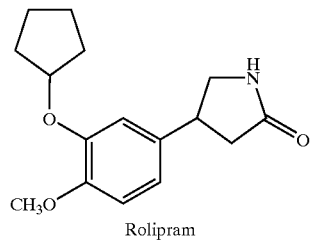
Rolipram

Investigators have continued to search for PDE4 inhibitors that are more selective with respect to inhibiting PDE4, that have a lower $IC_{50}$ than rolipram, and that avoid the undesirable central nervous system (CNS) side effects, such as retching, vomiting, and sedation, associated with the administration of rolipram. One class of compounds is disclosed in Feldman et al. U.S. Pat. No. 5,665,754. The compounds disclosed therein are substituted pyrrolidines having a structure similar to rolipram. One particular compound, having structural formula (I), has an $IC_{50}$ with respect to human recombinant PDE4 of about 2 nM. Inasmuch as a favorable separation of emetic side effect from efficacy was observed, these compounds did not exhibit a reduction in undesirable CNS effects.

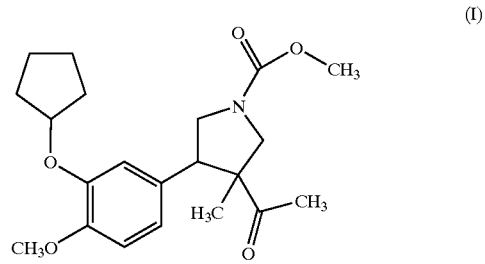

In addition, several companies are now undertaking clinical trials of other PDE4 inhibitors. However, problems relating to efficacy and adverse side effects, such as emesis and central nervous system disturbances, remain unsolved.

Accordingly, compounds that selectively inhibit PDE4, and that reduce or eliminate the adverse CNS side effects associated with prior PDE4 inhibitors, would be useful in the treatment of allergic and inflammatory diseases, and other diseases associated with excessive or unregulated production of cytokines, such as TNF. In addition, selective PDE4 inhibitors would be useful in the treatment of diseases that are associated with elevated cAMP levels or PDE4 function in a particular target tissue.

SUMMARY OF THE INVENTION

The present invention is directed to potent and selective PDE4 inhibitors useful in treatment of diseases and conditions where inhibition of PDE4 activity is considered beneficial. The present PDE4 inhibitors unexpectedly reduce or eliminate the adverse CNS side effects associated with prior PDE4 inhibitors.

In particular, the present invention is directed to compounds having the structural formula (II)

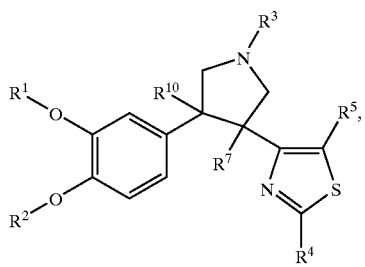

(II)

wherein $R^1$ is lower alkyl, bridged alkyl (e.g., norbornyl), aralkyl (e.g., indanyl), cycloalkyl, a 5- or 6-membered saturated heterocycle (e.g., 3-tetrahydrofuryl), $C_{1-3}$alkylenecycloalkyl (e.g., cyclopentylmethyl), aryl- or heteroaryl-substituted propargyl (e.g., —CH$_2$C≡C—C$_6$H$_5$), aryl- or heteroaryl-substituted allyl (e.g., —CH$_2$CH=CH—C$_6$H$_5$), or halocycloalkyl (e.g., fluorocyclopentyl);

$R^2$ is hydrogen, methyl, or halo-substituted methyl, e.g., CHF$_2$;

$R^3$ is selected from the group consisting of C(=O)OR$^7$, C(=O)R$^7$, C(=NH)NR$^8$R$^9$, C(=O)NR$^8$R$^9$, lower alkyl, bridged alkyl, cycloalkyl, haloalkyl, halocycloalkyl, $C_{1-3}$alkylenecycloalkyl, a 5- or 6-membered saturated heterocycle, aryl, heteroaryl, heteroarylSO$_2$, aralkyl, alkaryl, heteroaralkyl, heteroalkaryl, $C_{1-3}$alkyleneC(=O)OR$^7$, C(=O)$C_{1-3}$alkyleneC(=O)OR$^7$, $C_{1-3}$alkyleneheteroaryl, C(=O)C(=O)OR$^7$, C(=O)$C_{1-3}$alkyleneC(=O)OR$^7$, C(=O)$C_{1-3}$alkyleneNHC(=O)OR$^7$, C(=O)$C_{1-3}$alkyleneNH$_2$, and NHC(=O)OR$^7$;

$R^4$ is hydrogen, lower alkyl, haloalkyl, cycloalkyl, aryl, C(=O)R$^7$, OR$^8$, NR$^8$R$^9$, or SR$^8$;

$R^5$ is hydrogen, lower alkyl, haloalkyl, cycloalkyl, or aryl;

$R^7$ is selected from the group consisting of cycloalkyl, branched or unbranched lower alkyl, heteroaryl, a heterocycle, aralkyl, and aryl, and $R^7$ is optionally substituted with one or more of OR$^8$, NR$^8$R$^9$, or SR$^8$;

$R^8$ and $R^9$, same or different, are selected from the group consisting of hydrogen, lower alkyl, cycloalkyl, aryl, heteroaryl, alkaryl, heteroaralkyl, heteroalkaryl, and aralkyl, or $R^8$ and $R^9$ are taken together form a 4-membered to 7-membered ring;

$R^{10}$ is hydrogen, alkyl, haloalkyl, cycloalkyl, aryl, C(=O)alkyl, C(=O)cycloalkyl, C(=O)aryl, C(=O)Oalkyl, C(=O)Ocycloalkyl, C(=O)aryl, CH$_2$OH, CH$_2$Oalkyl, CHO, CN, NO$_2$, or SO$_2$R$^{11}$; and $R^{11}$ is alkyl, cycloalkyl, trifluoromethyl, aryl, aralkyl, or NR$^8$R$^9$.

The present invention also is directed to pharmaceutical compositions containing one or more of the compounds of structural formula (II), to use of the compounds and compositions containing the compounds in the treatment of a disease or disorder, and to methods of preparing compounds and intermediates involved in the synthesis of the compounds of structural formula (II).

The present invention also is directed to methods of treating a mammal having a condition where inhibition of PDE4 provides a benefit, of modulating CAMP levels in a mammal, of reducing TNFα levels in a mammal, of suppressing inflammatory cell activation in a mammal, and of inhibiting PDE4 function in a mammal by administering to the mammal a therapeutically effective amount of a compound of structural formula (II), or a composition containing a composition of structural formula (II).

DETAILED DESCRIPTION OF THE PREFERRED EMBODIMENTS

The present invention is directed to compounds having the structural formula (II):

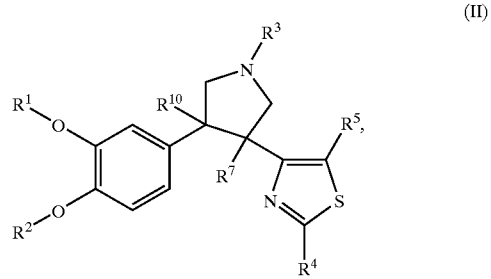

(II)

wherein $R^1$ is lower alkyl, bridged alkyl (e.g., norbornyl), aralkyl (e.g., indanyl), cycloalkyl, a 5- or 6-membered saturated heterocycle (e.g., 3-tetrahydrofuryl), Cl$_3$alkylenecycloalkyl (e.g., cyclopentylmethyl), aryl- or heteroaryl-substituted propargyl (i.e., —CH$_2$C≡C—C$_6$H$_5$), aryl- or heteroaryl-substituted allyl (e.g., —CH$_2$CH=CH—C$_6$H$_5$), or halocycloalkyl (e.g., fluorocyclopentyl);

$R^2$ is hydrogen, methyl, or halo-substituted methyl, e.g., CHF$_2$;

$R^3$ is selected from the group consisting of C(=O)OR$^7$, C(=O)R$^7$, C(=NH)NR$^8$R$^9$, C(=O)NR$^8$R$^9$, lower alkyl, bridged alkyl, cycloalkyl, haloalkyl, halocycloalkyl, $C_{1-3}$alkylenecycloalkyl, a 5- or 6-membered saturated heterocycle, aryl, heteroaryl, heteroarylSO$_2$, aralkyl, alkaryl, heteroaralkyl, heteroalkaryl, $C_{1-3}$alkyleneC(=O)OR$^7$, C(=O)$C_{1-3}$alkyleneC(=O)OR$^7$, $C_{1-3}$alkyleneheteroaryl, C(=O)C(=O)OR$^7$, C(=O)$C_{1-3}$alkyleneC(=O)OR$^7$, C(=O)$C_{1-3}$alkyleneNHC(=O)OR$^7$, C(=O)$C_{1-3}$alkyleneNH$_2$, and NHC(=O)OR$^7$;

$R^4$ is hydrogen, lower alkyl, haloalkyl, cycloalkyl, aryl, C(=O)R$^7$, OR$^8$, NR$^8$R$^9$, or SR$^8$;

$R^5$ is hydrogen, lower alkyl, haloalkyl, cycloalkyl, or aryl;

$R^7$ is selected from the group consisting of cycloalkyl, branched or unbranched lower alkyl, heteroaryl, a heterocycle, aralkyl, and aryl, and $R^7$ is optionally substituted with one or more of OR$^8$, NR$^8$R$^9$, or SR$^8$; and $R^8$ and $R^9$, same or different, are selected from the group consisting of hydrogen, lower alkyl, cycloalkyl, aryl, heteroaryl, alkaryl, heteroaralkyl, heteroalkaryl, and aralkyl, or $R^8$ and $R^9$ are taken together form a 4-membered to 7-membered ring;

$R^{10}$ is hydrogen, alkyl, haloalkyl, cycloalkyl, aryl, C(=O)alkyl, C(=O)cycloalkyl, C(=O)aryl, C(=O)Oalkyl, C(=O)Ocycloalkyl, C(=O)aryl, CH$_2$OH, CH$_2$Oalkyl, CHO, CN, NO$_2$, or SO$_2$R$^{11}$; and $R^{12}$ is alkyl, cycloalkyl, trifluoromethyl, aryl, aralkyl, or NR$^8$R$^9$.

A compound of structural formula (II) can be used alone, either neat or in a composition that further contains a pharmaceutically acceptable carrier. A compound of structural formula (II) also can be administering in conjunction with a second active therapeutic agent, for example, a second antiinflammatory therapeutic agent, like an agent capable of targeting TNFα.

Compounds of structural formula (II) can be used to modulate cAMP levels in a mammal, reduce TNFα levels in a mammal, suppress inflammatory cell activation in a mammal, inhibit PDE4 function in a mammal, and treat conditions afflicting a mammal where inhibition of PDE4 provides a benefit.

As used herein, the term "alkyl," alone or in combination, is defined to include straight chain and branched chain, and bridged, saturated hydrocarbon groups containing one to 16 carbon atoms. The term "lower alkyl" is defined herein as an alkyl group having one through six carbon atoms ($C_1$–$C_6$) Examples of lower alkyl groups include, but are not limited to, methyl, ethyl, n-propyl, isopropyl, isobutyl, n-butyl, neopentyl, n-hexyl, and the like. The term "alkynyl" refers to an unsaturated alkyl group that contains a carbon-carbon triple bond.

The term "bridged alkyl" is defined herein as a $C_6$–$C_{16}$ bicyclic or polycyclic hydrocarbon group, for example, norboryl, adamantyl, bicyclo[2.2.2]octyl, bicyclo[2.2.1] heptyl, bicyclo[3.2.1]octyl, or decahydronaphthyl.

The term "allyl" is defined herein as CH$_2$=CH—CH$_2$—, optionally substituted, e.g., alkyl or aryl substituted.

The term "propargyl" is defined herein as CH≡C—CH$_2$—, optionally substituted, e.g., alkyl or aryl substituted.

The term "cycloalkyl" is defined herein to include cyclic $C_3$–$C_7$ hydrocarbon groups. Examples of cycloalkyl groups include, but are not limited to, cyclopropyl, cyclobutyl, cyclohexyl, and cyclopentyl.

The term "alkylene" refers to an alkyl group having a substituent. For example, the term "$C_{1-3}$alkylenecycloalkyl" refers to an alkyl group containing one to three carbon atoms, and substituted with a cycloalkyl group.

The term "haloalkyl" is defined herein as an alkyl group substituted with one or more halo substituents, either fluoro, chloro, bromo, iodo, or combinations there-of. Similarly, "halocycloalkyl" is defined as a cycloalkyl group having one or more halo substituents.

The term "aryl," alone or in combination, is defined herein as a monocyclic or polycyclic aromatic group, preferably a monocyclic or bicyclic aromatic group, e.g., phenyl or naphthyl, that can be unsubstituted or substituted, for example, with one or more, and in particular one to three, substituents selected from halo, alkyl, hydroxy, hydroxyalkyl, alkoxy, aryloxy, aralkoxy, alkoxyalkyl, aryloxyalkyl, aralkoxyalkyl, haloalkyl, nitro, amino, alkylamino, acylamino, alkylthio, alkylsulfinyl, and alkylsulfonyl. Exemplary aryl groups include phenyl, naphthyl, tetrahydronaphthyl, 2-chlorophenyl, 3-chlorophenyl, 4-chlorophenyl, 2-methylphenyl, 4-methoxyphenyl, 3-trifluoromethylphenyl, 4-nitrophenyl, and the like.

The term "heteroaryl" is defined herein as a monocyclic or bicyclic ring system containing one or two aromatic rings and containing at least one nitrogen, oxygen, or sulfur atom in an aromatic ring, and which can be unsubstituted or substituted, for example, with one or more, and in particular one to three, substituents, like halo, alkyl, hydroxy, hydroxyalkyl, alkoxy, aryloxy, aralkoxy, alkoxyalkyl, aryloxyalkyl, aralkoxyalkyl, haloalkyl, nitro, amino, alkylamino, acylamino, alkylthio, alkylsulfinyl, and alkylsulfonyl. Examples of heteroaryl groups include thienyl, furyl, pyridyl, oxazolyl, quinolyl, isoquinolyl, indolyl, triazolyl, isothiazolyl, isoxazolyl, imidizolyl, benzothiazolyl, pyrazinyl, pyrimidinyl, thiazolyl, and thiadiazolyl.

The term "aralkyl" is defined herein as a previously defined alkyl group, wherein one of the hydrogen atoms is replaced by an aryl group as defined herein, for example, a phenyl group optionally having one or more substituents, for example, halo, alkyl, alkoxy, and the like. An example of an aralkyl group is a benzyl group.

The term "alkaryl" is defined herein as a previously defined aryl group, wherein one of the hydrogen atoms is replaced by an alkyl, cycloalkyl, haloalkyl, or halocycloalkyl group.

The terms "heteroaralkyl" and "heteroalkaryl" are defined similarly as the term "aralkyl" and "alkaryl," however, the aryl group is replaced by a heteroaryl group as previously defined.

The term "heterocycle" is defined as a 5- or 6-membered nonaromatic ring, optionally substituted, having one or more heteroatoms selected from oxygen, nitrogen, and sulfur present in the ring. Nonlimiting examples include tetrahydrofuran, piperidine, piperazine, sulfolane, morpholine, tetrahydropyran, dioxane, and the like.

The term "halogen" or "halo" is defined herein to include fluorine, chlorine, bromine, and iodine.

The terms "alkoxy," "aryloxy," and "aralkoxy" are defined as —OR, wherein R is alkyl, aryl, and aralkyl, respectively.

The term "alkoxyalkyl" is defined as an alkoxy group appended to an alkyl group. The terms "aryloxyalkyl" and "aralkoxyalkyl" are similarly defined as an aryloxy or aralkoxy group appended to an alkyl group.

The term "hydroxy" is defined as —OH.

The term "hydroxyalkyl" is defined as a hydroxy group appended to an alkyl group.

The term "amino" is defined as —NH$_2$.

The term "alkylamino" is defined as —NR$_2$ wherein at least one R is alkyl and the second R is alkyl or hydrogen.

The term "acylamino" is defined as RC(=O)N, wherein R is alkyl or aryl.

The term "nitro" is defined as —NO$_2$.

The term "alkylthio" is defined as —SR, where R is alkyl.

The term "alkylsulfinyl" is defined as R—SO$_2$, where R is alkyl.

The term "alkylsulfonyl" is defined as R—SO$_3$, where R is alkyl.

In preferred embodiments, R$^5$ is hydrogen, R$^7$ is methyl, R$^2$ is methyl or difluoromethyl, R$^4$ is selected from the group consisting of hydrogen, methyl, trifluoromethyl, cyclopropyl, acetyl, ethynyl, benzoyl, phenyl, and NR$^8$R$^9$, wherein R$^8$ and R$^9$, independently, are hydrogen, lower alkyl, or cycloalkyl, or are taken together to form a 5-membered or 6-membered ring. R$^1$ is selected from the group consisting of

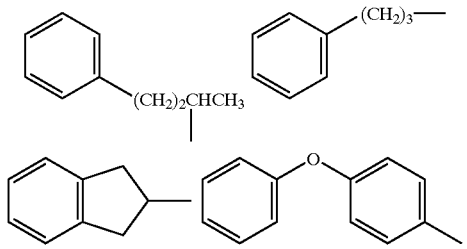

-continued

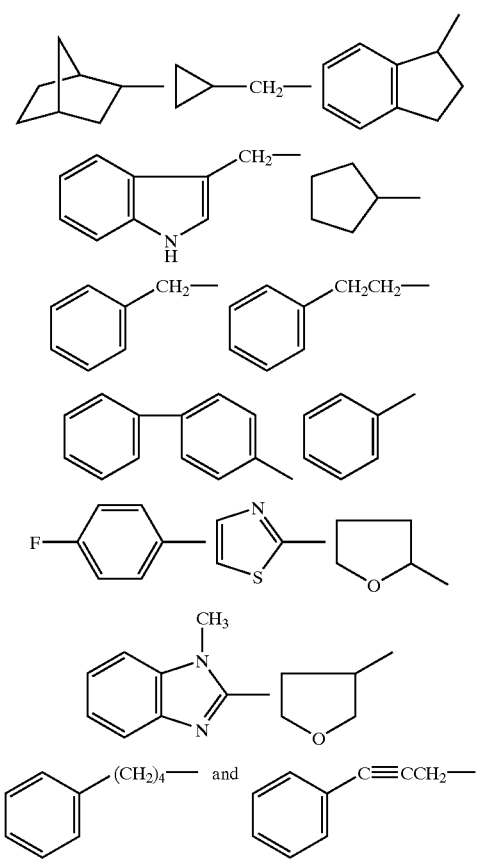

R[1] is selected from the group consisting of

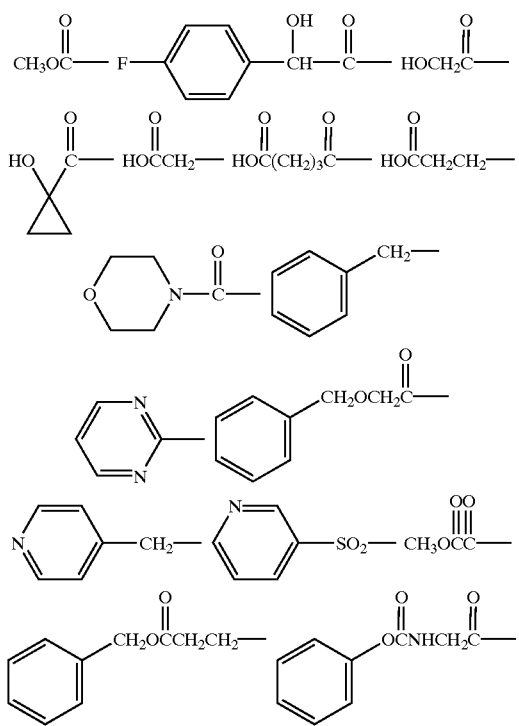

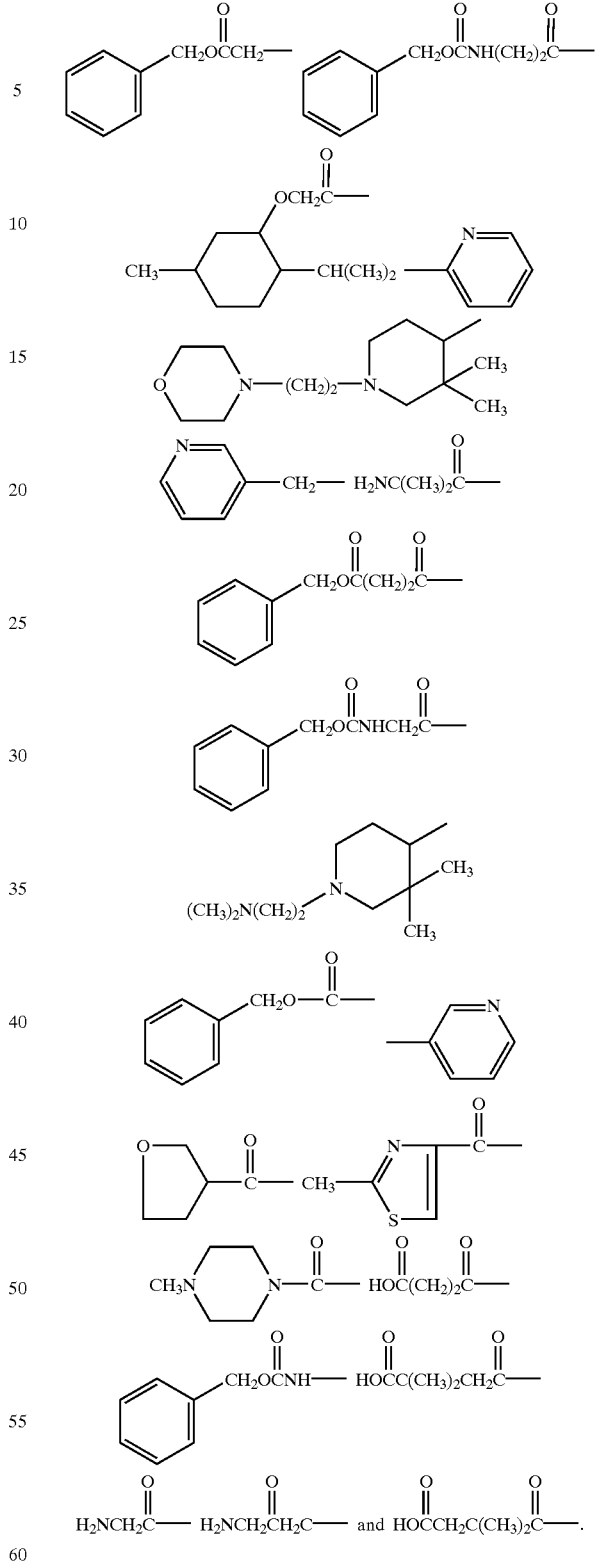

In most preferred embodiments, R[1] is selected from the group consisting of cyclopentyl, tetrahydrofuryl, indanyl, norbornyl, phenethyl, and phenylbutyl; R[2] is selected from the group consisting of methyl and difluoromethyl; R[3] is selected from the group consisting of $CO_2CH_3$, $C(=O)CH_2OH$, $C(=O)CH(CH_3)-OH$, $C(=O)C(CH_3)_2OH$, and

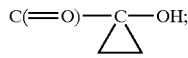

$R^4$ is $NR^8R^9$; $R^5$ is hydrogen; $R^7$ is methyl; $R^8$ and $R^9$, independently, are selected from the group consisting of hydrogen and lower alkyl, or are taken together form a 5-membered or 6-membered ring; and $R^{10}$ is hydrogen.

The present invention includes all possible stereoisomers and geometric isomers of compounds of structural formula (II), and includes not only racemic compounds but also the optically active isomers as well. When a compound of structural formula (II) is desire d as a single enantiomer, it can be obtained either by resolution of the final product or by stereospecific synthesis from either isomerically pure starting material or use of a chiral auxiliary reagent, for example, see Z. Ma et al., *Tetrahedron: Asymmetry*, 8(6), pages 883–888 (1997). Resolution of the final product, an intermediate, or a starting material can be achieved by any suitable method known in the art. Additionally, in situations where tautomers of the compounds of structural formula (II) are possible, the present invention is intended to include all tautomeric forms of the compounds. As demonstrated hereafter, specific stereoisomers exhibit an exceptional ability to inhibit PDE4 without manifesting the adverse CNS side effects typically associated with PDE4 inhibitors.

In particular, it is generally accepted that biological systems can exhibit very sensitive activities with respect to the absolute stereochemical nature of compounds. (See, E. J. Ariens, *Medicinal Research Reviews*, 6:451–466 (1986); E. J. Ariens, *Medicinal Research Reviews*, 7:367–387 (1987); K. W. Fowler, Handbook of Stereoisomers: Therapeutic Drugs, CRC Press, edited by Donald P. Smith, pp. 35–63 (1989); and S. C. Stinson, *Chemical and Engineering News*, 75:38–70 (1997).)

For example, rolipram is a stereospecific PDE4 inhibitor that contains one chiral center. The (−)-enantiomer of rolipram has a higher pharmacological potency than the (+)-enantiomer, which could be related to its potential antidepressant action. Schultz et al., *Naunyn-Schmiedeberg's Arch Pharmacol*, 333:23–30 (1986). Furthermore, the metabolism of rolipram appears stereospecific with the (+)-enantiomer exhibiting a faster clearance rate than the (−)-enantiomer. Krause et al., *Xenobiotica*, 18:561–571 (1988). Finally, a recent observation indicated that the (−)-enantiomer of rolipram (R-rolipram) is about ten-fold more emetic than the (+)-enantiomer (S-rolipram). A. Robichaud et al., *Neuropharmacology*, 38:289–297 (1999). This observation is not easily reconciled with differences in test animal disposition to rolipram isomers and the ability of rolipram to inhibit the PDE4 enzyme. The compounds of the present invention can have three chiral centers. As shown below, compounds of a specific stereochemical orientation exhibit similar PDE4 inhibitory activity and pharmacological activity, but altered CNS toxicity and emetic potential.

Accordingly, preferred compounds of the present invention have the structural formula (III):

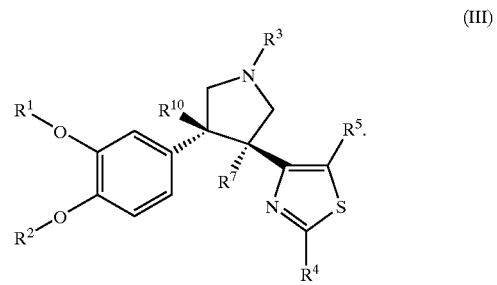

The compounds of structural formula (III) are potent and selective PDE4 inhibitors, and do not manifest the adverse CNS effects and emetic potential demonstrated by stereoisomers of a compound of structural formula (III).

Compounds of structural formula (II) which contain acidic moieties can form pharmaceutically acceptable salts with suitable cations. Suitable pharmaceutically acceptable cations include alkali metal (e.g., sodium or potassium) and alkaline earth metal (e.g., calcium or magnesium) cations. The pharmaceutically acceptable salts of the compounds of structural formula (II), which contain a basic center, are acid addition salts formed with pharmaceutically acceptable acids. Examples include the hydrochloride, hydrobromide, sulfate or bisulfate, phosphate or hydrogen phosphate, acetate, benzoate, succinate, fumarate, maleate, lactate, citrate, tartrate, gluconate, methanesulfonate, benzenesulphonate, and p-toluenesulphonate salts. In light of the foregoing, any reference to compounds of the present invention appearing herein is intended to include compounds of structural formula (II), as well as pharmaceutically acceptable salts and solvates thereof.

The compounds of the present invention can be therapeutically administered as the neat chemical, but it is preferable to administer compounds of structural formula (II) as a pharmaceutical composition or formulation. Accordingly, the present invention further provides for pharmaceutical formulations comprising a compound of structural formula (II), together with one or more pharmaceutically acceptable carriers and, optionally, other therapeutic and/or prophylactic ingredients. The carriers are "acceptable" in the sense of being compatible with the other ingredients of the formulation and not deleterious to the recipient thereof.

In particular, a selective PDE4 inhibitor of the present invention is useful alone or in combination with a second antiinflammatory therapeutic agent, for example, a therapeutic agent targeting TNFα, such as ENBREL® or REMICADE®, which have utility in treating rheumatoid arthritis. Likewise, therapeutic utility of IL-1 antagonism has also been shown in animal models for rheumatoid arthritis. Thus, it is envisioned that IL-1 antagonism, in combination with PDE4 inhibition, which attenuates TNFα, would be efficacious.

The present PDE4 inhibitors are useful in the treatment of a variety of allergic, autoimmune, and inflammatory diseases.

The term "treatment" includes preventing, lowering, stopping, or reversing the progression of severity of the condition or symptoms being treated. As such, the term "treatment" includes both medical therapeutic and/or prophylactic administration, as appropriate.

In particular, inflammation is a localized, protective response elicited by injury or destruction of tissues, which serves to destroy, dilute or wall off (i.e., sequester) both the injurious agent and the injured tissue. The term "inflammatory disease," as used herein, means any disease in which an excessive or unregulated inflammatory response leads to excessive inflammatory symptoms, host tissue damage, or loss of tissue function. Additionally, the term "autoimmune disease," as used herein, means any group of disorders in which tissue injury is associated with humoral or cell-mediated responses to the body's own constituents. The term "allergic disease," as used herein, means any symptoms, tissue damage, or loss of tissue function resulting from allergy. The term "arthritic disease," as used herein, means any of a large family of diseases that are characterized by inflammatory lesions of the joints attributable to a variety of etiologies. The term "dermatitis," as used herein, means any of a large family of diseases of the skin that are characterized by inflammation of the skin attributable to a variety of etiologies. The term "transplant rejection," as used herein, means any immune reaction directed against grafted tissue (including organ and cell (e.g., bone marrow)), characterized by a loss of function of the grafted and surrounding tissues, pain, swelling, leukocytosis and thrombocytopenia.

The present invention also provides a method of modulating cAMP levels in a mammal, as well as a method of treating diseases characterized by elevated cytokine levels.

The term "cytokine," as used herein, means any secreted polypeptide that affects the functions of other cells, and that modulates interactions between cells in the immune or inflammatory response. Cytokines include, but are not limited to monokines, lymphokines, and chemokines regardless of which cells produce them. For instance, a monokine is generally referred to as being produced and secreted by a monocyte, however, many other cells produce monokines, such as natural killer cells, fibroblasts, basophils, neutrophils, endothelial cells, brain astrocytes, bone marrow stromal cells, epidermal keratinocytes, and B-lymphocytes. Lymphokines are generally referred to as being produced by lymphocyte cells. Examples of cytokines include, but are not limited to, interleukin-1 (IL-1), interleukin-6 (IL-6), Tumor Necrosis Factor alpha (TNFα), and Tumor Necrosis Factor beta (TNFβ).

The present invention further provides a method of reducing TNF levels in a mammal, which comprises administering an effective amount of a compound of structural formula (II) to the mammal. The term "reducing TNF levels," as used herein, means either:

a) decreasing excessive in vivo TNF levels in a mammal to normal levels or below normal levels by inhibition of the in vivo release of TNF by all cells, including but not limited to monocytes or macrophages; or b) inducing a down-regulation, at the translational or transcription level, of excessive in vivo TNF levels in a mammal to normal levels or below normal levels; or c) inducing a down-regulation, by inhibition of the direct synthesis of TNF as a postranslational event.

Moreover, the compounds of the present invention are useful in suppressing inflammatory cell activation. The term "inflammatory cell activation," as used herein, means the induction by a stimulus (including, but not limited to, cytokines, antigens or auto-antibodies) of a proliferative cellular response, the production of soluble mediators (including but not limited to cytokines, oxygen radicals, enzymes, prostanoids, or vasoactive amines), or cell surface expression of new or increased numbers of mediators (including, but not limited to, major histocompatability antigens or cell adhesion molecules) in inflammatory cells (including but not limited to monocytes, macrophages, T lymphocytes, B lymphocytes, granulocytes, polymorphonuclear leukocytes, mast cells, basophils, eosinophils, dendritic cells, and endothelial cells). It will be appreciated by persons skilled in the art that the activation of one or a combination of these phenotypes in these cells can contribute to the initiation, perpetuation, or exacerbation of an inflammatory condition.

The compounds of the present invention also are useful in causing airway smooth muscle relaxation, bronchodilation, and prevention of bronchoconstriction.

The compounds of the present invention, therefore, are useful in treating such diseases as arthritic diseases (such as rheumatoid arthritis), osteoarthritis, gouty arthritis, spondylitis, thyroid-associated ophthalmopathy, Behcet disease, sepsis, septic shock, endotoxic shock, gram negative sepsis, gram positive sepsis, toxic shock syndrome, asthma, chronic bronchitis, allergic rhinitis, allergic conjunctivitis, vernal conjunctivitis, eosinophilic granuloma, adult (acute) respiratory distress syndrome (ARDS), chronic pulmonary inflammatory disease (such as chronic obstructive pulmonary disease), silicosis, pulmonary sarcoidosis, reperfusion injury of the myocardium, brain or extremities, brain or spinal cord injury due to minor trauma, fibrosis including cystic fibrosis, keloid formation, scar tissue formation, atherosclerosis, autoimmune diseases, such as systemic lupus erythematosus (SLE) and transplant rejection disorders (e.g., graft vs. host (GvH) reaction and allograft rejection), chronic glomerulonephritis, inflammatory bowel diseases, such as Crohn's disease and ulcerative colitis, proliferative lymphocytic diseases, such as leukemias (e.g. chronic lymphocytic leukemia; CLL) (see Mentz et al., *Blood* 88, pp. 2172–2182 (1996)), and inflammatory dermatoses, such as atopic dermatitis, psoriasis, or urticaria.

Other examples of such diseases or related conditions include cardiomyopathies, such as congestive heart failure, pyrexia, cachexia, cachexia secondary to infection or malignancy, cachexia secondary to acquired immune deficiency syndrome (AIDS), ARC(AIDS-related complex), cerebral malaria, osteoporosis and bone resorption diseases, and fever and myalgias due to infection. In addition, the compounds of the present invention are useful in the treatment of diabetes insipidus and central nervous system disorders, such as depression and multi-infarct dementia.

Compounds of the present invention also have utility outside of that typically known as therapeutic. For example, the present compounds can function as organ transplant preservatives (see Pinsky et al., *J. Clin. Invest.*, 92, pp. 2994–3002 (1993)) as well.

Selective PDE4 inhibitors also can be useful in the treatment of erectile dysfunction, especially vasculogenic impotence (Doherty, Jr. et al. U.S. Pat. No. 6,127,363), diabetes insipidus (*Kidney Int.*, 37, p. 362, (1990); *Kidney Int.*, 35, p. 494, (1989)) and central nervous system disorders, such as multiinfarct dementia (Nicholson, *Psychopharmacology*, 101, p. 147 (1990)), depression (Eckman et al., *Curr. Ther. Res.*, 43, p. 291 (1988)), anxiety and stress responses (*Neuropharmacology*, 38, p. 1831 (1991)), cerebral ischemia (*Eur. J. Pharmacol.*, 272, p. 107 (1995)), tardive dyskinesia (*J. Clin. Pharmocol.*, 16, p. 304 (1976)), Parkinson's disease (see *Neurology*, 25, p. 722 (1975); *Clin. Exp. Pharmacol, Physiol.*, 26, p. 421 (1999)), and premenstrual syndrome. With respect to depression, PDE4-selective inhibitors show efficacy in a variety of animal models of depression such as the "behavioral despair" or Porsolt tests (*Eur. J. Pharmacol.*, 47, p. 379 (1978); *Eur. J. Pharmacol.*, 57, p. 431 (1979); Antidepressants: neurochemical, behavioral and clinical prospectives, Enna, Malick, and Richelson, eds., *Raven Press*, p. 121 (1981)), and the "tail suspension test"

(*Psychopharmacology*, 85, p. 367 (1985)). Recent research findings show that chronic in vivo treatment by a variety of antidepressants increase the brain-derived expression of PDE4 (J. Neuroscience, 19, p. 610 (1999)). Therefore, a selective PDE4 inhibitor can be used alone or in conjunction with a second therapeutic agent in a treatment for the four major classes of antidepressants: electroconvulsive procedures, monoamine oxidase inhibitors, and selective reuptake inhibitors of serotonin or norepinephrine. Selective PDE4 inhibitors also can be useful in applications that modulate bronchodilatory activity via direct action on bronchial smooth muscle cells for the treatment of asthma.

Compounds and pharmaceutical compositions suitable for use in the present invention include those wherein the active ingredient is administered to a mammal in an effective amount to achieve its intended purpose. More specifically, a "therapeutically effective amount" means an amount effective to prevent development of, or to alleviate the existing symptoms of, the subject being treated. Determination of the effective amounts is well within the capability of those skilled in the art, especially in light of the detailed disclosure provided herein.

The term "mammal" as used herein includes males and females, and encompasses humans, domestic animals (e.g., cats, dogs), livestock (e.g., cattle, horses, swine), and wildlife (e.g., primates, large cats, zoo specimens).

A "therapeutically effective dose" refers to that amount of the compound that results in achieving the desired effect. Toxicity and therapeutic efficacy of such compounds can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index, which is expressed as the ratio between $LD_{50}$ and $ED_{50}$. Compounds which exhibit high therapeutic indices are preferred. The data obtained from such data can be used in formulating a dosage range for use in humans. The dosage of such compounds preferably lies within a range of circulating concentrations that include the $ED_{50}$ with little or no toxicity. The dosage can vary within this range depending upon the dosage form employed, and the route of administration utilized.

The exact formulation, route of administration, and dosage can be chosen by the individual physician in view of the patient's condition. Dosage amount and interval can be adjusted individually to provide plasma levels of the active moiety which are sufficient to maintain the therapeutic effects.

As appreciated by persons skilled in the art, reference herein to treatment extends to prophylaxis, as well as to treatment of established diseases or symptoms. It is further appreciated that the amount of a compound of the invention required for use in treatment varies with the nature of the condition being treated, and with the age and the condition of the patient, and is ultimately determined by the attendant physician or veterinarian. In general, however, doses employed for adult human treatment typically are in the range of 0.001 mg/kg to about 100. mg/kg per day. The desired dose can be conveniently administered in a single dose, or as multiple doses administered at appropriate intervals, for example as two, three, four or more subdoses per day. In practice, the physician determines the actual dosing regimen which is most suitable for an individual patient, and the dosage varies with the age, weight, and response of the particular patient. The above dosages are exemplary of the average case, but there can be individual instances in which higher or lower dosages are merited, and such are within the scope of the present invention.

Formulations of the present invention can be administered in a standard manner for the treatment of the indicated diseases, such as orally, parenterally, transmucosally (e.g., sublingually or via buccal administration), topically, transdermally, rectally, via inhalation (e.g., nasal or deep lung inhalation). Parenteral administration includes, but is not limited to intravenous, intraarterial, intraperitoneal, subcutaneous, intramuscular, intrathecal, and intraarticular. Parenteral administration also can be accomplished using a high pressure technique, like POWDERJECT™.

For buccal administration, the composition can be in the form of tablets or lozenges formulated in conventional manner. For example, tablets and capsules for oral administration can contain conventional excipients such as binding agents (for example, syrup, accacia, gelatin, sorbitol, tragacanth, mucilage of starch or polyvinylpyrrolidone), fillers (for example, lactose, sugar, microcrystalline, cellulose, maize-starch, calcium phosphate or sorbitol), lubricants (for example, magnesium, stearate, stearic acid, talc, polyethylene glycol or silica), disintegrants (for example, potato starch or sodium starch glycollate), or wetting agents (for example, sodium lauryl sulfate). The tablets can be coated according to methods well known in the art.

Alternatively, the compounds of the present invention can be incorporated into oral liquid preparations such as aqueous or oily suspensions, solutions, emulsions, syrups, or elixirs, for example. Moreover, formulations containing these compounds can be presented as a dry product for constitution with water or other suitable vehicle before use. Such liquid preparations can contain conventional additives, such as suspending agents, such as sorbitol syrup, methyl cellulose, glucose/sugar syrup, gelatin, hydroxyethylcellulose, hydroxypropylmethylcellulose, carboxymethyl cellulose, aluminum stearate gel, and hydrogenated edible fats; emulsifying agents, such as lecithin, sorbitan monooleate, or acacia; nonaqueous vehicles (which can include edible oils), such as almond oil, fractionated coconut oil, oily esters, propylene glycol, and ethyl alcohol; and preservatives, such as methyl or propyl p-hydroxybenzoate and sorbic acid.

Such preparations also can be formulated as suppositories, e.g., containing conventional suppository bases, such as cocoa butter or other glycerides. Compositions for inhalation typically can be provided in the form of a solution, suspension, or emulsion that can be administered as a dry powder or in the form of an aerosol using a conventional propellant, such as dichlorodifluoromethane or trichlorofluoromethane. Typical topical and transdermal formulations comprise conventional aqueous or nonaqueous vehicles, such as eye drops, creams, ointments, lotions, and pastes, or are in the form of a medicated plaster, patch, or membrane.

Additionally, compositions of the present invention can be formulated for parenteral administration by injection or continuous infusion. Formulations for injection can be in the form of suspensions, solutions, or emulsions in oily or aqueous vehicles, and can contain formulation agents, such as suspending, stabilizing, and/or dispersing agents. Alternatively, the active ingredient can be in powder form for constitution with a suitable vehicle (e.g., sterile, pyrogen-free water) before use.

A composition in accordance with the present invention also can be formulated as a depot preparation. Such long acting formulations can be administered by implantation (for example, subcutaneously or intramuscularly) or by intramuscular injection. Accordingly, the compounds of the invention can be formulated with suitable polymeric or hydrophobic materials (e.g., an emulsion in an acceptable oil), ion exchange resins, or as sparingly soluble derivatives (e.g., a sparingly soluble salt).

For veterinary use, a compound of formula (II), or nontoxic salts thereof, is administered as a suitably acceptable formulation in accordance with normal veterinary practice. The veterinarian can readily determine the dosing regimen and route of administration that is most appropriate for a particular animal.

Thus, the invention provides in a further aspect a pharmaceutical composition comprising a compound of the formula (II), together with a pharmaceutically acceptable diluent or carrier therefor. There is further provided by the present invention a process of preparing a pharmaceutical composition comprising a compound of formula (II), which process comprises mixing a compound of formula (II), together with a pharmaceutically acceptable diluent or carrier therefor.

A specific, nonlimiting example of a compound of structural formula (II) is provided below, the synthesis of which was performed in accordance with the procedure set forth below.

Generally, compounds of structural formula (II) can be prepared according to the following synthetic scheme. In the scheme described below, it is understood in the art that protecting groups can be employed where necessary in accordance with general principles of synthetic chemistry. These protecting groups are removed in the final steps of the synthesis under basic, acidic, or hydrogenolytic conditions which are readily apparent to those skilled in the art. By employing appropriate manipulation and protection of any chemical functionalities, synthesis of compounds of structural formula (II) not specifically set forth herein can be accomplished by methods analogous to the schemes set forth below.

Unless otherwise noted, all starting materials were obtained from commercial suppliers and used without further purification. All reactions and chromatography fractions were analyzed by thinlayer chromatography on 250-mm silica gel plates, visualized with UV (ultraviolet) light or $I_2$ (iodine) stain. Products and intermediates were purified by flash chromatography, or reverse-phase HPLC.

The compounds of general structural formula (II) can be prepared, for example, as set forth in the following Example 1. Other synthetic routes also are known to persons skilled in the art. The following reaction scheme provides a compound of structural formula (II), wherein $R^1$ and $R^2$, i.e., cyclopentyl and $CH_3$, are determined by the starting materials. Proper selection of other starting materials, or performing conversion reactions on intermediates and examples, provide compounds of general structural formula (II) having other recited $R^1$ through $R^{11}$ substituents. The following example is provided for illustration and should not be construed as limiting.

EXAMPLE 1

Preparation of (3S,4R)-4-(3-Cyclopentyloxy-4-methoxyphenyl)-3-methyl-3-(2-methylaminothiazol-4-yl)pyrrolidine-1-carboxylic Acid Methyl Ester

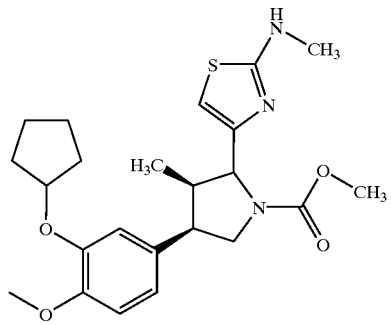

To a solution of 1-methyl-2-thiourea (0.038 g, 0.418 mmol) in methanol (1 mL), at 50° C., was added a solution of (3S,4R)-3-(2-bromoethanoyl)-4-(3-cyclopentyloxy-4-methoxyphenyl)-3-methyl-pyrrolidine-1-carboxylic acid methyl ester (0.19 g, 0.42 mmol) in methanol (1 mL). The temperature was raised to 70° C. and refluxed for 2 hours. The reaction mixture then was concentrated under reduced pressure and dissolved in acetonitrile-water ($CH_3CN$—$H_2O$) (1 mL) for purification by HPLC on a C18 column (Luna 10μ, C18, 250×10 mm). Gradient elution of 50–100% acetonitrile-water (0.05% TFA) yielded the named product as a white powder after lyophilization (91 mg, 49%).

$^1$H NMR (300 MHz, $CDCl_3$) δ (ppm) 11.84 (s,1H, NH) 6.95–6.70 (m, 3H, aromatic), 6.14 (m, 1H, aromatic), 4.87–4.82 (br. m, 1H), 3.97–3.5 (m, 4H), 3.84 (s, 3H, $OCH_3$), 3.78 (s, 3H, $OCH_3$), 3. 40–3.36 (m, 1H) 3.05 (s, 3H, $NCH_3$), 2.0–1.6 (m, 8H, cyclopentyl) 1.07 (s, 3H, $CH_3$)

The compounds of structural formula (II) were tested for an ability to inhibit PDE4. The ability of a compound to inhibit PDE4 activity is related to the $IC_{50}$ value for the compound, i.e., the concentration of inhibitor required for 50% inhibition of enzyme activity. The $IC_{50}$ value for compounds of structural formula (II) were determined using recombinant human PDE4.

The compounds of the present invention typically exhibit an $IC_{50}$ value against recombinant human PDE4 of less than about 100 μM, and preferably less than about 50 μM, and more preferably less than about 25 μm. The compounds of the present invention typically exhibit an $IC_{50}$ value against recombinant human PDE4 of less than about 5 μM, and often less than about 1 μM. To achieve the full advantage of the present invention, a present PDE4 inhibitor has an $IC_{50}$ of about 0.05 μM to about 15 μM.

The $IC_{50}$ values for the compounds were determined from concentration-response curves typically using concentrations ranging from 0.1 pM to 500 μM. Tests against other PDE enzymes using standard methodology, as described in Loughney et al., *J. Biol. Chem.*, 271, pp. 796–806 (1996), also showed that compounds of the present invention are highly selective for the cAMP-specific PDE4 enzyme.

The production of recombinant human PDEs and the $IC_{50}$ determinations can be accomplished by well-known methods in the art. Exemplary methods are described as follows:

EXPRESSION OF HUMAN PDEs

Expression in Baculovirus-Infected *Spodoptera fugiperda* (Sf9) Cells

Baculovirus transfer plasmids were constructed using either pBlueBacIII (Invitrogen) or pFastBac (BRL-Gibco). The structure of all plasmids was verified by sequencing across the vector junctions and by fully sequencing all regions generated by PCR. Plasmid pBB-PDE1A3/6 contained the complete open reading frame of PDE1A3 (Loughney et al., *J. Biol. Chem.*, 271, pp. 796–806 (1996)) in pBlue-BacIII. Plasmid Hcam3aBB contained the complete open reading frame of PDE1C3 (Loughney et al. (1996)) in pBlueBacIII. Plasmid pBB-PDE3A contained the complete open reading frame of PDE3A (Meacci et al., *Proc. Natl. Acad. Sci., USA*, 89, pp. 3721–3725 (1992)) in pBlue-BacIII.

Recombinant virus stocks were produced using either the MaxBac system (Invitrogen) or the FastBac system (Gibco-BRL) according to the manufacturer's protocols. In both cases, expression of recombinant human PDEs in the resultant viruses was driven off the viral polyhedron promoter.

When using the MaxBac® system, virus was plaque purified twice in order to insure that no wild type (occ+) virus contaminated the preparation. Protein expression was carried out as follows. Sf9 cells were grown at 27° C. in Grace's Insect culture medium (Gibco-BRL) supplemented with 10% fetal bovine serum, 0.33% TC yeastolate, 0.33% lactalbumin hydrolysate, 4.2 mM $NaHCO_3$, 10 µg/mL gentamycin, 100 units/mL penicillin, and 100 µg/mL streptomycin. Exponentially growing cells were infected at a multiplicity of approximately 2 to 3 virus particles per cell and incubated for 48 hours. Cells were collected by centrifugation, washed with nonsupplemented Grace's medium, and quick-frozen for storage.

Expression in *Sacdharomyces cerevisiae* (Yeast)

Recombinant production of human PDE1B, PDE2, PDE4A, PDE4B, PDE4C, PDE4D, PDE5, and PDE7 was carried out similarly to that described in Example 7 of U.S. Pat. No. 5,702,936, incorporated herein by reference, except that the yeast transformation vector employed, which is derived from the basic ADH2 plasmid described in Price et al., *Methods in Enzymology*, 185, pp. 308–318 (1990), incorporated yeast ADH2 promoter and terminator sequences and the Saccharomyces cerevisiae host was the protease-deficient strain BJ2–54 deposited on Aug. 31, 1998 with the American Type Culture Collection, Manassas, Va., under accession number ATCC 74465. Transformed host cells were grown in 2X SC-leu medium, pH 6.2, with trace metals, and vitamins. After 24 hours, YEP medium-containing glycerol was added to a final concentration of 2X YET/3% glycerol. Approximately 24 hr later, cells were harvested, washed, and stored at −70° C.

HUMAN PHOSPHODIESTERASE PREPARATIONS

Phosphodiesterase Activity Determinations

Phosphodiesterase activity of the preparations was determined as follows. PDE assays utilizing a charcoal separation technique were performed essentially as described in Louahney et al. (1996). In this assay, PDE activity converts [32P]cAMP or [32P]cGMP to the corresponding [32P]5'-AMP or [32P]5'-GMP in proportion to the amount of PDE activity present. The [32P]5'-AMP or [32P]5'-GMP then was quantitatively converted to free [32P]phosphate and unlabeled adenosine or guanosine by the action of snake venom 5'-nucleotidase. Hence, the amount of [32P]phosphate liberated is proportional to enzyme activity. The assay was performed at 30° C. in a 100 µL reaction mixture containing (final concentrations) 40 nM Tris HCl (pH 8.0), 1 µM $ZnSO_4$, 5 mM $MgCl_2$, and 0.1 mg/mL bovine serum albumin (BSA). Alternatively, in assays assessing PDE1-specific activity, incubation mixtures further incorporated the use of 0.1 mM $CaCl_2$ and 10 µg/mL calmodulin. PDE enzyme was present in quantities that yield <30% total hydrolysis of substrate (linear assay conditions). The assay was initiated by addition of substrate (1 mM [32P]cAMP or cGMP), and the mixture was incubated for 12 minutes. Seventy-five (75) µg of Crotalus atrox venom then was added, and the incubation was continued for 3 minutes (15 minutes total). The reaction was stopped by addition of 200 µL of activated charcoal (25 mg/mL suspension in 0.1 M $NaH_2PO_4$, pH 4). After centrifugation (750×g for 3 minutes) to sediment the charcoal, a sample of the supernatant was taken for radioactivity determination in a scintillation counter and the PDE activity was calculated.

Inhibitor analyses were performed similarly to the method described in Loughney et al., *J. Biol. Chem.*, 271, pp. 796–806 (1996), except both cGMP and cAMP were used, and substrate concentrations were kept below 32 nM, which is far below the Km of the tested PDEs.

Human PDE4A, 4B, 4C, 4D Preparations

Preparation of PDE4A from *S. cerevisiae*.

Yeast cells (50 g of yeast strain YI26 harboring HDUN1.46) were thawed at room temperature by mixing with 50 mL of Lysis Buffer (50 mM MOPS pH 7.5, 10 µM $ZnSO_4$, 2 mM $MgCl_2$, 14.2 mM 2-mercaptoethanol, 5 µg/mL each of pepstatin, leupeptin, aprotinin, 20 µg/mL each of calpain inhibitors I and II, and 2 mM benzamidine HCl). Cells were lysed in a French® pressure cell (SLM-Aminco®, Spectronic Instruments) at 10° C. The extract was centrifuged in a Beckman JA-10 rotor at 9,000 rpm for 22 minutes at 4° C. The supernatant was removed and centrifuged in a Beckman TI45 rotor at 36,000 rpm for 45 minutes at 4° C.

PDE4A was precipitated from the high-speed supernatant by the addition of solid ammonium sulfate (0.26 g/mL supernatant) while stirring in an ice bath and maintaining the pH between 7.0 and 7.5. The precipitated proteins containing PDE4A were collected via centrifugation in a Beckman JA-10 rotor at 9,000 rpm for 22 minutes. The precipitate was resuspended in 50 mL of Buffer G (50 mM MOPS pH 7.5, 10 µM $ZnSO_4$, 5 mM $MgCl_2$, 100 mM NaCl, 14.2 mM 2-mercaptoethanol, 2 mM benzamidine HCl, 5 µg/mL each of leupeptin, pepstatin, and aprotinin, and 20 µg/mL each of calpain inhibitors I and II) and passed through a 0.45 µm filter.

The resuspended sample (50 to 100 mL) was loaded onto a 5×100 cm column of Pharmacia SEPHACRYL® S-300 equilibrated in Buffer G. Enzyme activity was eluted at a flow rate of 2 mL/min and pooled for later fractionation.

The PDE4A isolated from gel filtration chromatography was applied to a 1.6×20 cm column of Sigma Cibacron Blue Agarose-type 300 (10 mL) equilibrated in Buffer A (50 mM MOPS pH 7.5, 10 µM $ZnSO_4$, 5 mM $MgCl_2$, 14.2 mM 2-mercaptoethanol, and 100 mM benzamidine HCl). The column was washed in succession with 50 to 100 mL of Buffer A, 20 to 30 mL of Buffer A containing 20 mM 5'-AMP, 50 to 100 mL of Buffer A containing 1.5 M NaCl, and 10 to 20 mL of Buffer C(50 mM Tris HCl pH 8, 10 µM $ZnSO_4$, 14.2 mM 2-mercaptoethanol, and 2 mM benzamidine HCl). The enzyme was eluted with 20 to 30 mL of Buffer C containing 20 mM cAMP.

The PDE activity peak was pooled, and precipitated with ammonium sulfate (0.33 g/mL enzyme pool) to remove excess cyclic nucleotide. The precipitated proteins were resuspended in Buffer X (25 mM MOPS pH 7.5, 5 µM $ZnSO_4$, 50 mM NaCl, 1 mM DTT, and 1 mM benzamidine HCl), and desalted via gel filtration on a Pharmacia PD-10® column per manufacturer's instructions. The enzyme was quick-frozen in a dry ice/ethanol bath and stored at −70° C.

The resultant preparations were about >80% pure by SDS-PAGE. These preparations had specific activities of about 10 to 40 µmol cAMP hydrolyzed per minute per milligram protein.

Preparation of PDE4B from *S. cerevisiae*

Yeast cells (150 g of yeast strain YI23 harboring HDUN2.32) were thawed by mixing with 100 mL glass beads (0.5 mM, acid washed) and 150 mL Lysis Buffer (50 mM MOPS pH 7.2, 2 mM EDTA, 2 mM EGTA, 1 mM DTT, 2 mM benzamidine HCl, 5 µg/mL each of pepstatin, leupeptin, .aprotinin, calpain inhibitors I and II) at room temperature. The mixture was cooled to 4° C., transferred to a Bead-Beater®, and the cells lysed by rapid mixing for 6 cycles of 30 seconds each. The homogenate was centrifuged for 22 minutes in a Beckman J2-21M centrifuge using a JA-10 rotor at 9,000 rpm and 4° C. The supernatant was recovered and centrifuged in a Beckman XL-80 ultracentrifuge using a TI45 rotor at 36,000 rpm for 45 minutes at 4° C. The supernatant was recovered and PDE4B was precipitated by the addition of solid ammonium sulfate (0.26 g/mL supernatant) while stirring in an ice bath and maintaining the pH between 7.0 and 7.5. This mixture was then centrifuged for 22 minutes in a Beckman J2 centrifuge using a JA-10 rotor at 9,000 rpm (12,000×g). The supernatant was discarded and the pellet was dissolved in 200 mL of Buffer A (50 mM MOPS pH 7.5, 5 mM $MgCl_2$, 1 mM DTT, 1 mM benzamidine HCl, and 5 µg/mL each of leupeptin, pepstatin, and aprotinin). The pH and conductivity were corrected to 7.5 and 15–20 mS, respectively.

The resuspended sample was loaded onto a 1.6×200 cm column (25 mL) of Sigma Cibacron Blue Agarose-type 300 equilibrated in Buffer A. The sample was cycled through the column 4 to 6 times over the course of 12 hours. The column was washed in succession with 125 to 250 mL of Buffer A, 125 to 250 mL of Buffer A containing 1.5 M NaCl, and 25 to 50 mL of Buffer A. The enzyme was eluted with 50 to 75 mL of Buffer E (50 mM Tris HCl pH 8, 2 mM EDTA, 2 mM EGTA, 1 mM DTT, 2 mM benzamidine HCl, and 20 mM cAMP) and 50 to 75 mL of Buffer E containing 1 M NaCl. The PDE activity peak was pooled, and precipitated with ammonium sulfate (0.4 g/mL enzyme pool) to remove excess cyclic nucleotide. The precipitated proteins were resuspended in Buffer X (25 mM MOPS pH 7.5, 5 µM $ZnSO_4$, 50 mM NaCl, 1 mM DTT, and 1 mM benzamidine HCl) and desalted via gel filtration on a Pharmacia PD-10® column per manufacturer's instructions. The enzyme pool was dialyzed overnight against Buffer X containing 50% glycerol. This enzyme was quick-frozen in a dry ice/ethanol bath and stored at −70° C.

The resultant preparations were about >90% pure by SDS-PAGE. These preparations had specific activities of about 10 to 50 µmol cAMP hydrolyzed per minute per milligram protein.

Preparation of PDE4C from *S. cerevisiae*

Yeast cells (150 g of yeast strain YI30 harboring HDUN3.48) were thawed by mixing with 100 mL glass beads (0.5 mM, acid washed) and 150 mL Lysis Buffer (50 mM MOPS pH 7.2, 2 mM EDTA, 2 mM EGTA, 1 mM DTT, 2 mM benzamidine HCl, 5 µg/mL each of pepstatin, leupeptin, aprotinin, calpain inhibitors I and II) at room temperature. The mixture was cooled to 40° C., transferred to a BEAD-BEATER®, and the cells lysed by rapid mixing for 6 cycles of 30 sec each. The homogenate was centrifuged for 22 minutes in a Beckman J2–21M centrifuge using a JA-10 rotor at 9,000 rpm and 4° C. The supernatant was recovered and centrifuged in a Beckman XL-80 ultracentrifuge using a TI45 rotor at 36,000 rpm for 45 minutes at 4° C.

The supernatant was recovered and PDE4C was precipitated by the addition of solid ammonium sulfate (0.26 g/mL supernatant) while stirring in an ice bath and maintaining the pH between 7.0 and 7.5. Thirty minutes later, this mixture was centrifuged for 22 minutes in a Beckman J2 centrifuge using a JA-10 rotor at 9,000 rpm (12,000×g). The supernatant was discarded and the pellet was dissolved in 200 mL of Buffer A (50 mM MOPS pH 7.5, 5 mM $MgCl_2$, 1 mM DTT, 2 mM benzamidine HCl, and 5 µg/mL each of leupeptin, pepstatin, and aprotinin). The pH and conductivity were corrected to 7.5 and 15–20 mS, respectively.

The resuspended sample was loaded onto a 1.6×20 cm column (25 mL) of Sigma Cibacron Blue Agarose-type 300 equilibrated in Buffer A. The sample was cycled through the column 4 to 6 times over the course of 12 hours. The column was washed in succession with 125 to 250 mL of Buffer A, 125 to 250 mL of Buffer A containing 1.5 M NaCl, and then 25 to 50 mL of Buffer A. The enzyme was eluted with 50 to 75 mL of Buffer E (50 mM Tris HCl pH 8, 2 mM EDTA, 2 mM EGTA, 1 mM DTT, 2 mM benzamidine HCl, and 20 mM cAMP) and 50 to 75 mL of Buffer E containing 1 M NaCl. The PDE4C activity peak was pooled, and precipitated with ammonium sulfate (0.4 g/mL enzyme pool) to remove excess cyclic nucleotide. The precipitated proteins were resuspended in Buffer X (25 mM MOPS pH 7.2, 5 µM $ZnSO_4$, 50 mM NaCl, 1 mM DTT, and 1 mM benzamidine HCl) and desalted via gel filtration on a Pharmacia PD-10® column per manufacturer's instructions. The enzyme pool was dialyzed overnight against Buffer X containing 50% glycerol. This enzyme was quick-frozen in a dry ice/ethanol bath and stored at −70° C.

The resultant preparations were about >80% pure by SDS-PAGE. These preparations had specific activities of about 10 to 20 µmol cAMP hydrolyzed per minute per milligram protein.

Preparation of PDE4D from *S. cerevisiae*

Yeast cells (100 g of yeast strain YI29 harboring HDUN4.11) were thawed by mixing with 150 mL glass beads (0.5 mM, acid washed) and 150 mL Lysis Buffer (50 mM MOPS pH 7.2, 10 µM $ZnSO_4$, 2 mM $MgCl_2$, 14.2 mM 2-mercaptoethanol, 2 mM benzamidine HCl, 5 µg/mL each of pepstatin, leupeptin, aprotinin, calpain inhibitors I and II) at room temperature. The mixture was cooled to 4° C., transferred to a Bead-Beater®, and the cells lysed by rapid mixing for 6 cycles of 30 sec each. The homogenate was centrifuged for 22 minutes in a Beckman J2-21M centrifuge using a JA-10 rotor at 9,000 rpm and 4° C. The supernatant was recovered and centrifuged in a Beckman XL-80 ultracentrifuge using a TI45 rotor at 36,000 rpm for 45 minutes at 4° C. The supernatant was recovered and PDE4D was precipitated by the addition of solid ammonium sulfate (0.33 g/mL supernatant) while stirring in an ice bath and maintaining the pH between 7.0 and 7.5. Thirty minutes later, this mixture was centrifuged for 22 minutes in a Beckman J2 centrifuge using a JA-10 rotor at 9,000 rpm (12,000×g). The supernatant was discarded and the pellet was dissolved in 100 mL of Buffer A (50 mM MOPS pH 7.5, 10 µM $ZnSO_4$, 5 mM $MgCl_2$, 14.2 mM 2-mercaptoethanol, 100 mM benzamidine HCl, and 5 µg/mL each of leupeptin, pepstatin, aprotinin, calpain inhibitor I and II). The pH and conductivity were corrected to 7.5 and 15–20 mS, respectively.

At a flow rate of 0.67 mL/min, the resuspended sample was loaded onto a 1.6×20 cm column (10 mL) of Sigma Cibacron Blue Agarose-type 300 equilibrated in Buffer A. The column was washed in succession with 50 to 100 mL of Buffer A, 20 to 30 mL of Buffer A containing 20 mM 5'-AMP, 50 to 100 mL of Buffer A containing 1.5 M NaCl, and then 10 to 20 mL of Buffer C(50 mM Tris HCl pH 8, 10

μM ZnSO$_4$, 14.2 mM 2-mercaptoethanol, 2 mM benzamidine HCl). The enzyme was eluted with 20 to 30 mL of Buffer C containing 20 mM cAMP.

The PDE4D activity peak was pooled and precipitated with ammonium sulfate (0.4 g/mL enzyme pool) to remove excess cyclic nucleotide. The precipitated proteins were resuspended in Buffer X (25 mM MOPS pH 7.2, 5 μM ZnSO$_4$, 50 mM NaCl, 1 mM DTT, and 1 mM benzamidine HCl) and desalted via gel filtration on a Pharmacia PD-10® column per manufacturer's instructions. The enzyme pool was dialyzed overnight against Buffer X containing 50% glycerol. This enzyme preparation was quick-frozen in a dry ice/ethanol bath and stored at −70° C.

The resultant preparations were about >80% pure by SDS-PAGE. These preparations had specific activities of about 20 to 50 μmol cAMP hydrolyzed per minute per milligram protein.

| Example No. | Molecular Weight | PDE4 IC$_{50}$ (nM) |
| --- | --- | --- |
| 1 | 445.58 | 4,731.1 |

The data presented above shows that the present compounds are potent inhibitors of PDE4, e.g., the compounds have an IC$_{50}$ vs. human recombinant PDE4 of about 0.05 μM to about 15 μM. Preferred compounds have an IC$_{50}$ of about 100 μM or less, and especially preferred compounds have an IC$_{50}$ of about 50 μM or less.

The compounds of the present invention are useful for selectively inhibiting PDE4 activity in a mammal, without exhibiting the adverse CNS and emetic effects associated with prior PDE4 inhibitors.

Obviously, many modifications and variations of the invention as hereinbefore set forth can be made without departing from the spirit and scope thereof and, therefore, only such limitations should be imposed as are indicated by the appended claims.

What is claimed is:

1. A method of inhibiting IL-1β release by monocytes in a mammal comprising administering to said mammal a therapeutically effective amount of a compound having a formula:

wherein R$^1$ is lower alkyl, bridged alkyl, aralkyl, cycloalkyl, a 5- or 6-membered saturated heterocycle, C$_{1-3}$alkylenecycloalkyl, aryl- or heteroaryl-substituted propargyl, aryl- or heteroaryl-substituted allyl, or halocycloalkyl;

R$^2$ is hydrogen, methyl, or halo-substituted methyl;

R$^3$ is selected from the group consisting of C(=O)OR$^7$, C(=O)R$^7$, C(=NH)NR$^8$R$^9$, C(=O)NR$^8$R$^9$, lower alkyl, bridged alkyl, cycloalkyl, haloalkyl, halocycloalkyl, C$_{1-3}$alkylenecycloalkyl, a substituted or unsubstituted 5- or 6-membered saturated heterocycle, aryl, heteroaryl, heteroarylSO$_2$, aralkyl, alkaryl, heteroaralkyl, heteroalkaryl, C$_{1-3}$alkyleneC(=O)OR$^7$, C(=O)C$_{1-3}$alkyleneC(=O)OR$^7$, C$_{1-3}$alkyleneheteroaryl, C(=O)C(=O)OR$^7$, C(=O)C$_{1-3}$alkyleneC(=O)OR$^7$, C(=O)C$_{1-3}$alkyleneNHC(=O)OR$^7$, C(=O)C$_{1-3}$alkyleneNH$_2$, and NHC(=O)OR$^7$;

R$^4$ is hydrogen, lower alkyl, haloalkyl, cycloalkyl, aryl, C(=O)R$^7$, OR$^8$, NR$^8$R$^9$, or SR$^8$;

R$^5$ is hydrogen, lower alkyl, haloalkyl, cycloalkyl, or aryl;

R$^7$ is selected from the group consisting of cycloalkyl, branched or unbranched lower alkyl, heteroaryl, aryl, a substituted or unsubstituted heterocycle, and substituted or unsubstituted aralkyl, and R$^7$ is optionally substituted with one or more of RO$^8$, NR$^8$R$^9$, or SR$^8$; and R$^8$ and R$^9$, same or different, are selected from the group consisting of hydrogen, lower alkyl, cycloalkyl, aryl, heteroaryl, alkaryl, heteroaralkyl, heteroalkaryl, and aralkyl, or R$^8$ and R$^9$ are taken together form a 4-membered to 7-membered ring;

R$^{10}$ is hydrogen, alkyl, haloalkyl, cycloalkyl, aryl, C(=O)alkyl, C(=O)cycloalkyl, C(=O)aryl, C(=O)Oalkyl, C(=O)Ocycloalkyl, C(=O)aryl, CH$_2$OH, CH$_2$Oalkyl, CHO, CN, NO$_2$, or SO$_2$R$^{11}$; and R$^{11}$ is alkyl, cycloalkyl, trifluoromethyl, aryl, aralkyl, or NR$^8$R$^9$.

2. The method of claim 1 having a structure:

3. The method of claim 1 having a formula:

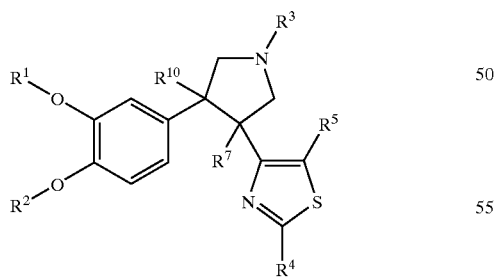

4. A method of inhibiting activation of human T-lymphocytes in a mammal comprising administering to said mammal a therapeutically effective amount of a compound having a formula:

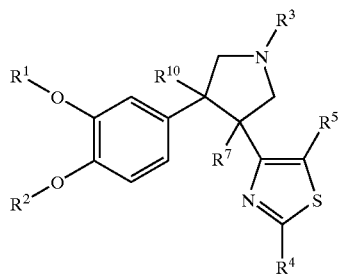

wherein $R^1$ is lower alkyl, bridged alkyl, aralkyl, cycloalkyl, a 5- or 6-membered saturated heterocycle, $C_{1-3}$alkylenecycloalkyl, aryl- or heteroaryl-substituted propargyl, aryl- or heteroaryl-substituted allyl, or halocycloalkyl;

$R^2$ is hydrogen, methyl, or halo-substituted methyl;

$R^3$ is selected from the group consisting of $C(=O)OR^7$, $C(=O)R^7$, $C(=NH)NR^8R^9$, $C(=O)NR^8R^9$, lower alkyl, bridged alkyl, cycloalkyl, haloalkyl, halocycloalkyl, $C_{1-3}$alkylenecycloalkyl, a substituted or unsubstituted 5- or 6-membered saturated heterocycle, aryl, heteroaryl, heteroarylSO$_2$, aralkyl, alkaryl, heteroaralkyl, heteroalkaryl, $C_{1-3}$ alkyleneC$(=O)OR^7$, $C(=O)C_{1-3}$alkyleneC$(=O)OR^7$, $C_{1-3}$alkyleneheteroaryl, $C(=O)C(=O)OR^7$, $C(=O)C_{1-3}$alkyleneC$(=O)OR^7$, $C(=O)C_{1-3}$alkyleneNHC$(=O)OR^7$, $C(=O)C_{1-3}$alkyleneNH$_2$, and NHC$(=O)OR^7$;

$R^4$ is hydrogen, lower alkyl, haloalkyl, cycloalkyl, aryl, $C(=O)R^7$, $OR^8$, $NR^8R^9$, or $SR^8$;

$R^5$ is hydrogen, lower alkyl, haloalkyl, cycloalkyl, or aryl;

$R^7$ is selected from the group consisting of cycloalkyl, branched or unbranched lower alkyl, heteroaryl, aryl, a substituted or unsubstituted heterocycle, and substituted or unsubstituted aralkyl, and $R^7$ is optionally substituted with one or more of $RO^8$, $NR^8R^9$, or $SR^8$; and $R^8$ and $R^9$, same or different, are selected from the group consisting of hydrogen, lower alkyl, cycloalkyl, aryl, heteroaryl, alkaryl, heteroaralkyl, heteroalkaryl, and aralkyl, or $R^8$ and $R^9$ are taken together form a 4-membered to 7-membered ring;

$R^{10}$ is hydrogen, alkyl, haloalkyl, cycloalkyl, aryl, $C(=O)$alkyl, $C(=O)$cycloalkyl, $C(=O)$aryl, $C(=O)$Oalkyl, $C(=O)$Ocycloalkyl, $C(=O)$aryl, $CH_2OH$, $CH_2O$alkyl, CHO, CN, $NO_2$, or $SO_2R^{11}$; and $R^{11}$ is alkyl, cycloalkyl, trifluoromethyl, aryl, aralkyl, or $NR^8R^9$.

5. A pharmaceutical composition comprising
(a) a compound having a formula

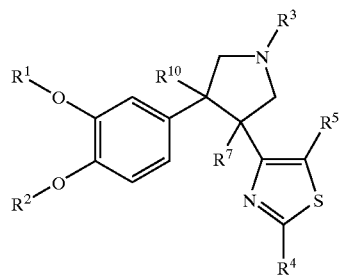

wherein $R^1$ is lower alkyl, bridged alkyl, aralkyl, cycloalkyl, a 5- or 6-membered saturated heterocycle, $C_{1-3}$alkylenecycloalkyl, aryl- or heteroaryl-substituted propargyl, aryl- or heteroaryl-substituted allyl, or halocycloalkyl;

$R^2$ is hydrogen, methyl, or halo-substituted methyl;

$R^3$ is selected from the group consisting of $C(=O)OR^7$, $C(=O)R^7$, $C(=NH)NR^8R^9$, $C(=O)NR^8R^9$, lower alkyl, bridged alkyl, cycloalkyl, haloalkyl, halocycloalkyl, $C_{1-3}$alkylenecycloalkyl, a substituted or unsubstituted 5- or 6-membered saturated heterocycle, aryl, heteroaryl, heteroarylSO$_2$, aralkyl, alkaryl, heteroaralkyl, heteroalkaryl, $C_{1-3}$ alkylenec$(=O)OR^7$, $C(=O)C_{1-3}$alkyleneC$(=O)OR^7$, $C_{1-3}$alkyleneheteroaryl, $C(=O)C(=O)OR^7$, $C(=O)C_{1-3}$alkyleneC$(=O)OR^7$, $C(=O)C_{1-3}$alkyleneNHC$(=O)OR^7$, $C(=O)C_{1-3}$alkyleneNH$_2$, and NHC$(=O)OR^7$;

$R^4$ is hydrogen, lower alkyl, haloalkyl, cycloalkyl, aryl, $C(=O)R^7$, $OR^8$, $NR^8R^9$, or $SR^8$;

$R^5$ is hydrogen, lower alkyl, haloalkyl, cycloalkyl, or aryl;

$R^7$ is selected from the group consisting of cycloalkyl, branched or unbranched lower alkyl, heteroaryl, aryl, a substituted or unsubstituted heterocycle, and substituted or unsubstituted aralkyl, and $R^7$ is optionally substituted with one or more of $RO^8$, $NR^8R^9$, or $SR^8$; and $R^8$ and $R^9$, same or different, are selected from the group consisting of hydrogen, lower alkyl, cycloalkyl, aryl, heteroaryl, alkaryl, heteroaralkyl, heteroalkaryl, and aralkyl, or $R^8$ and $R^9$ are taken together form a 4-membered to 7-membered ring;

$R^{10}$ is hydrogen, alkyl, haloalkyl, cycloalkyl, aryl, $C(=O)$alkyl, $C(=O)$cycloalkyl, $C(=O)$aryl, $C(=O)$Oalkyl, $C(=O)$Ocycloalkyl, $C(=O)$aryl, $CH_2OH$, $CH_2O$alkyl, CHO, CN, $NO_2$, or $SO_2R^{11}$; and $R^{11}$ is alkyl, cycloalkyl, trifluoromethyl, aryl, aralkyl, or $NR^8R^9$;

(b) a pharmaceutically acceptable carrier, and
(c) a second therapeutic agent having utility in the treatment of rheumatoid arthritis.

* * * * *

UNITED STATES PATENT AND TRADEMARK OFFICE
CERTIFICATE OF CORRECTION

PATENT NO. : 6,486,186 B2
DATED : November 26, 2002
INVENTOR(S) : Fowler et al.

It is certified that error appears in the above-identified patent and that said Letters Patent is hereby corrected as shown below:

Title page,
Item [56], References Cited, OTHER PUBLICATIONS, "Verghese et al." reference, "*Cardiiol.*" should be -- *Cardiol.* --; and "Dhillon et al." reference, "1995)" should be -- (1995) --

Column 3,
Line 59, "anti-in-flammatory" should be -- anti-inflammatory --

Column 6,
Line 31, "Cl$_3$alkylenecycloalkyl" should be -- C$_{1-3}$ alkylenecycloalkyl --
Line 50, "$_{OR}{}^8$," should be -- OR$^8$, --
Line 66, "R$^{12}$" should be -- R$^{11}$ --

Column 7,
Line 42, "there-of." should be -- thereof. --

Column 11,
Line 17, "desire d" should be -- desired --

Column 14,
Line 36, "ARC(AIDS-related" should be -- ARC  (AIDS-related --

Column 15,
Line 59, "100. mg/kg" should be -- 100 mg/kg --

Column 18,
Line 13, "$\delta$ (ppm)" should be -- $\delta$ (ppm) : --

Column 19,
Lines 39 and 40, "Louahney et al." should be -- Loughney et al. --

UNITED STATES PATENT AND TRADEMARK OFFICE
CERTIFICATE OF CORRECTION

PATENT NO.    : 6,486,186 B2
DATED         : November 26, 2002
INVENTOR(S)   : Fowler et al.

It is certified that error appears in the above-identified patent and that said Letters Patent is hereby corrected as shown below:

Column 21,
Line 1, ".aprotinin," should be -- aprotinin --
Line 53, "40ºC" -- should be -- 4ºC --

Signed and Sealed this

Tenth Day of June, 2003

JAMES E. ROGAN
*Director of the United States Patent and Trademark Office*